United States Patent
Zu et al.

(10) Patent No.: US 12,241,111 B2
(45) Date of Patent: Mar. 4, 2025

(54) USE OF GALACTURONATE AND OR GALACTURONATE POLYMERS IN CONJUNCTION WITH CARBOHYDRATES TO CONTROL METABOLIC STATE OF ORGANISMS

(71) Applicant: U.S. Army DEVCOM Army Research Laboratory, Adelphi, MD (US)

(72) Inventors: Theresah N. K. Zu, Elkridge, MD (US); Christian J. Sund, Bethesda, MD (US); Sanchao Liu, Ellicott City, MD (US); Elliot S. Gerlach, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 701 days.

(21) Appl. No.: 17/376,613

(22) Filed: Jul. 15, 2021

(65) Prior Publication Data

US 2021/0340580 A1    Nov. 4, 2021

Related U.S. Application Data

(62) Division of application No. 16/418,618, filed on May 21, 2019, now Pat. No. 11,091,783.

(51) Int. Cl.
| | | |
|---|---|---|
| C12P 7/54 | (2006.01) | |
| C12N 1/20 | (2006.01) | |
| C12P 7/52 | (2006.01) | |

(52) U.S. Cl.
CPC ............... *C12P 7/54* (2013.01); *C12N 1/20* (2013.01); *C12P 7/52* (2013.01)

(58) Field of Classification Search
CPC .............. C12P 7/54; C12P 7/52; C12N 1/20
See application file for complete search history.

(56) References Cited

U.S. PATENT DOCUMENTS

| 11,091,783 B2 | 8/2021 | Zu et al. |
| 2019/0032003 A1 | 1/2019 | Park et al. |

FOREIGN PATENT DOCUMENTS

| WO | 2018067458 | 4/2018 |

OTHER PUBLICATIONS

Vasconcelos, I., Girbal, L., and Soucaille, P. Regulatino of Carbon and Electron Flow in Clostridium acetobutylicum Grown in Chemostat Culture at Neutral pH on Mixtures of Glucose and Glycerol. Journal of Bacteriology, Mar. 1994. https://doi.org/10.1128/jb.176.5.1443-1450. 1994 (Year: 1994).*

(Continued)

*Primary Examiner* — Louise W Humphrey
*Assistant Examiner* — Rachel Emily Martin
(74) *Attorney, Agent, or Firm* — Eric B. Compton

(57) ABSTRACT

A method of producing chemicals includes providing fermentative cells; co-feeding any of galacturonate and galacturonate polymers with carbohydrates to the fermentative cells; and producing a chemical from the fermentative cells. The fermentative cells may include any of *Clostridium acetobutylicum* and *Clostridium saccharoperbutylacetonicum*. The carbohydrates may include any of glucose, mannose, galactose, fructose, arabinose, xylose, sucrose, lactose, maltose, cellobiose, and starch. The method may include providing a substantially equal proportion of the any of galacturonate and galacturonate polymers and the carbohydrates for co-feeding to the fermentative cells. The method may include altering a proportion of the any of galacturonate and galacturonate polymers to the carbohydrates. The method may include modulating a production of the chemical by altering the proportion of the any of galacturonate and galacturonate polymers to the carbohydrates. The chemical may include any of acetate and butyrate.

17 Claims, 15 Drawing Sheets

(56) References Cited

OTHER PUBLICATIONS

Protzko, R.J., Latimer, L.N., Martinho, Z. et al. Engineering Saccharomyces cerevisiae for co-utilization of D-galacturonic acid and D-glucose from citrus peel waste. Nat Commun 9, 5059 (2018). https://doi.org/10.1038/s41467-018-07589-w (Year: 2018).*

Servinsky, M. D., Liu, S., Gerlach, E. S., Germane, K. L., & Sund, C. J., "Fermentation of oxidized hexose derivatives by Clostridium acetobutylicum." Microbial Cell Factories 2014, 13:139.

Poster titled: "A holistic study of a C. acetobutylicum fermentation for intracellular and extracellular metabolites output." Theresah N. K. Zu, Sanchao Liu, Elliot S. Gerlach, and Christian J. Sund (displayed Feb. 28, 2018 at the Pittcon Conference and Expo 2018, Orlando, Florida).

Poster titled: "Tailored Feedstock for Controlled Chemical Production." Theresah N. K. Zu, Katherine L. Germane, Sanchao Liu, Elliot S. Gerlach, Rebecca Renberg, and Christian J. Sund. (displayed May 29, 2018 in the Zahl Building hallway at the U.S. Army Research Library in Adelphi, MD as part of the Synthetic Biology for Military Environments (SBME) Applied Research for Advancement of Priorities (ARAP) mid-year review tour).

Poster titled: "Synthetic Biology and Feedstock Regulation for Controlled Microbial Chemical Production in C. acetobutylicum." Theresah Zu, Katherine Germane, Sanchao Liu, Elliot Gerlach, Rebecca Renberg, and Christian Sund. (displayed Sep. 25-27, 2018 at the Synthetic Biology for Defense Workshop (SB4D), Arlington, VA).

U.S. Appl. No. 15/939,329, filed Mar. 29, 2018, titled: "Administration of Tailored Feedstock to Increase Antibiotic Susceptibility." Inventors: Christian J. Sund and Katherine L. Germane.

U.S. Appl. No. 16/258,780, filed Jan. 28, 2019, titled: "Administration of Tailored Feedstock to Increase Nitro-Containing Amphenicol Antibiotic Susceptibility." Inventors: Katherine L. Germane and Christian J. Sund.

Junyoung O. Park, et al., "Synergistic substrate cofeeding stimulates reductive metabolism," Nature Metabolism vol. 1, pp. 643-651 (2019).

* cited by examiner

C. acetobutylicum

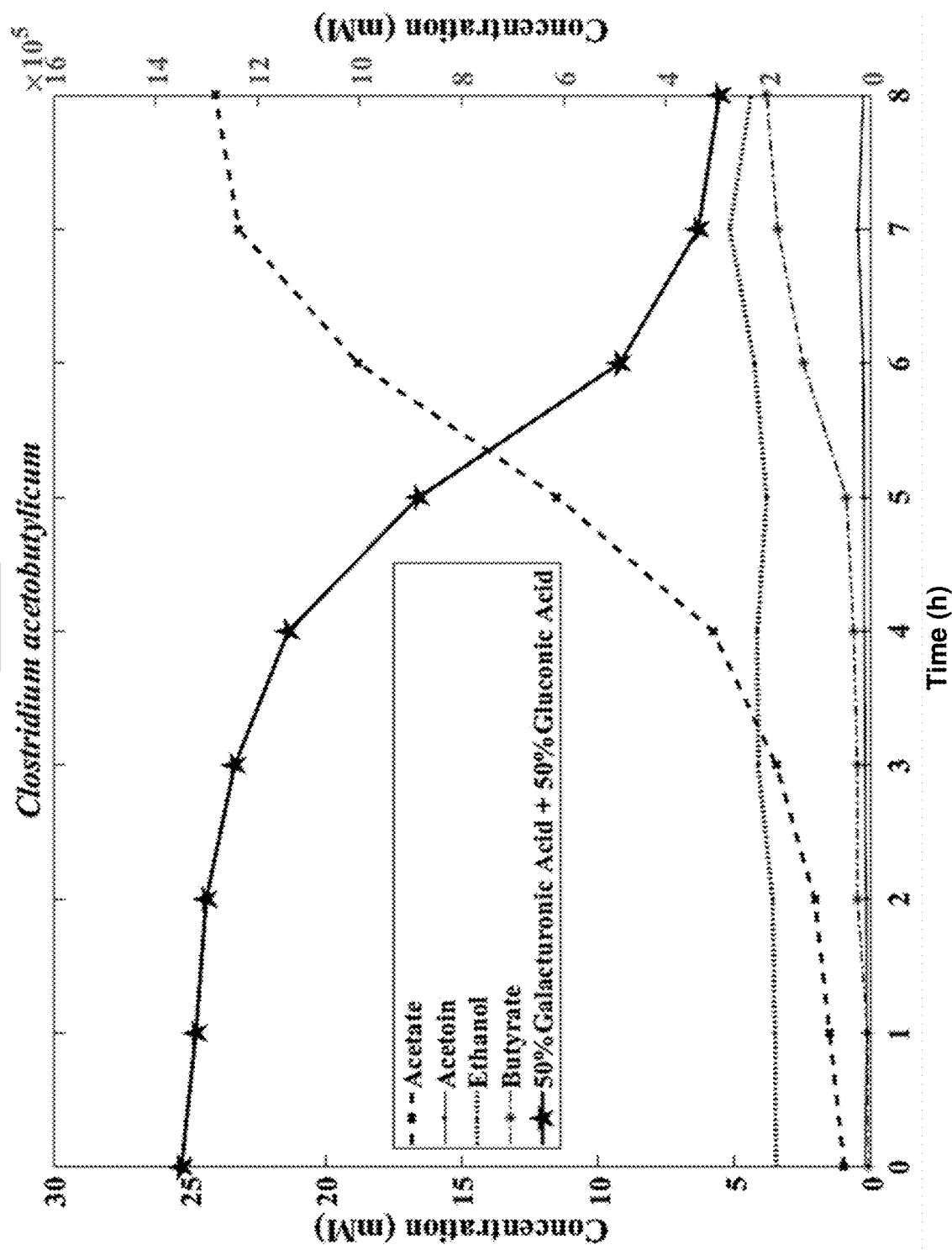
FIG. 7A *Clostridium acetobutylicum*

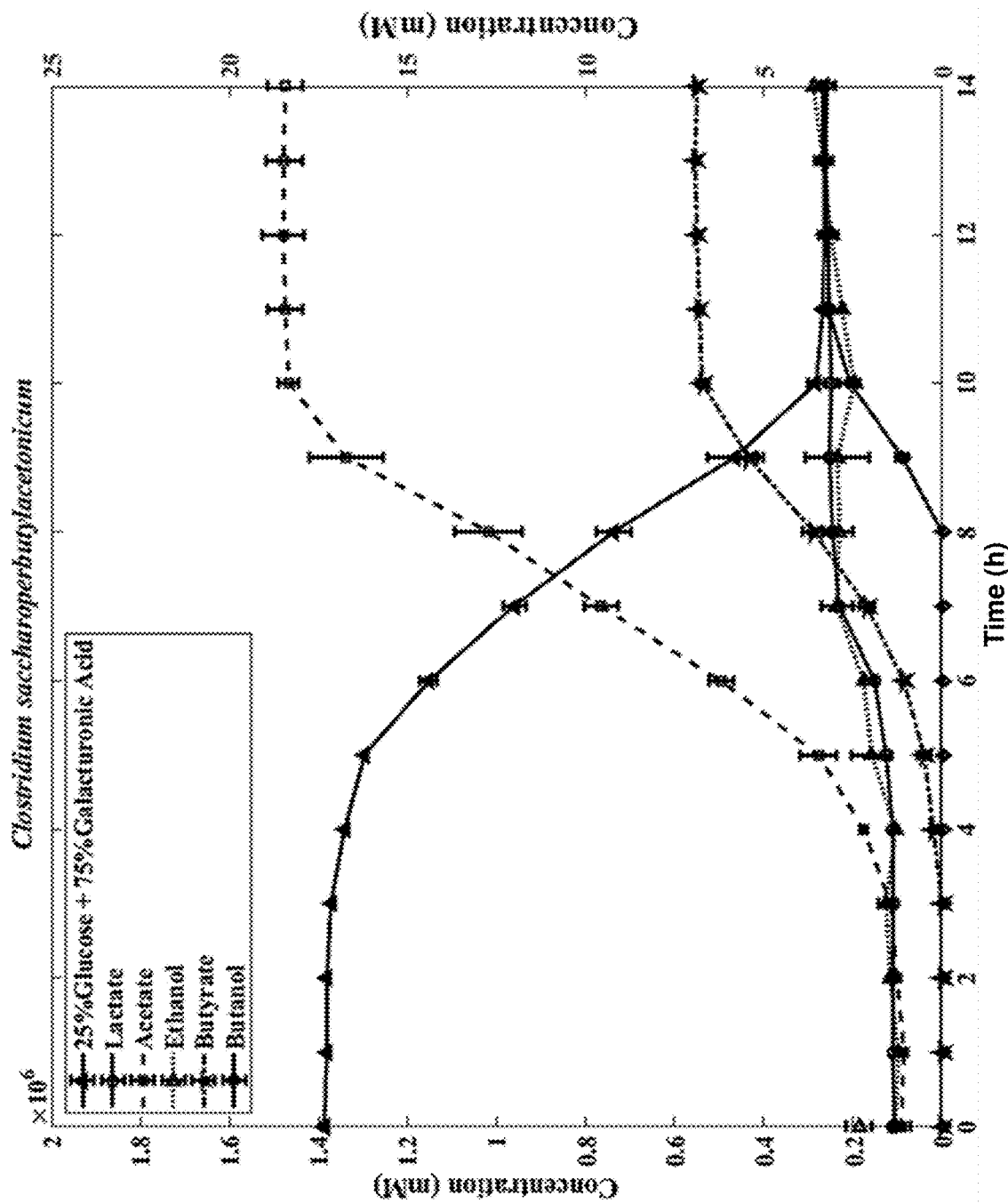

USE OF GALACTURONATE AND OR GALACTURONATE POLYMERS IN CONJUNCTION WITH CARBOHYDRATES TO CONTROL METABOLIC STATE OF ORGANISMS

RELATED APPLICATION INFORMATION

This application is a divisional of U.S. patent application Ser. No. 16/418,618, filed May 21, 2019, the disclosure of which is herein incorporated by reference in its entirety for all purposes.

GOVERNMENT INTEREST

The embodiments herein may be manufactured, used, and/or licensed by or for the United States Government without the payment of royalties thereon.

BACKGROUND

Technical Field

The embodiments herein generally relate to metabolic engineering and bioinformatics.

Description of the Related Art

Traditionally, fermentation studies have focused on improving product yields. Factors that contribute to increased yield include substrate utilization, metabolic pathway and redox state of the cells. In fermentations with *Clostridium acetobutylicum*, acids (acetic and butyric) produced in the acidogenic phase are later converted to solvents (acetone, butanol and ethanol) in the second phase during solventogenesis. To effectively improve on fermentation processes, researchers are exploring a systems biology approach to make these microbial processes more flexible, configurable, fast, and robust. Generally, current processing technologies are not amenable to complex inputs such as waste materials, and are also unable to create complex hierarchical structures with extreme precision. Also, synthetic chemistry is generally incapable of producing certain high value products where biology can naturally. However, more studies are needed to fully understand metabolic pathways in biological systems to this effect. Finally, most investigated synthetic pathways are studied in non-robust chassis that fail to withstand harsh terrains.

Fermentative organisms are known to adjust their metabolite state when fed on substrates with different oxidation states by altering production of reduced electron carriers such as NADH and/or NADPH. Moreover, the production of chemicals using microorganisms often requires metabolic engineering to insert chemical production pathways and/or provide the necessary metabolic flux to the pathway for sufficient chemical production. One challenge in this process is providing the correct proportion of carbon-containing precursors and redox cofactors in the correct oxidation state to the enzymes in the desired pathway.

SUMMARY

In view of the foregoing, an embodiment herein provides a method of producing chemicals, the method comprising providing fermentative cells; co-feeding any of galacturonate and galacturonate polymers with carbohydrates to the fermentative cells; and producing a chemical from the fermentative cells. The fermentative cells may comprise any of *Clostridium acetobutylicum* and *Clostridium saccharoperbutylacetonicum*. The carbohydrates may comprise any of glucose, mannose, galactose, fructose, arabinose, xylose, sucrose, lactose, maltose, cellobiose, and starch.

The method may comprise providing a substantially equal proportion of the any of galacturonate and galacturonate polymers and the carbohydrates for co-feeding to the fermentative cells. The method may comprise altering a proportion of the any of galacturonate and galacturonate polymers to the carbohydrates. The method may comprise modulating a production of the chemical by altering the proportion of the any of galacturonate and galacturonate polymers to the carbohydrates. The chemical may comprise acetate. The chemical may comprise butyrate.

Another embodiment provides a method of controlling a metabolic process, the method comprising providing an anaerobic organism; providing a first chemical substrate comprising a first oxidation state; providing a second chemical substrate comprising a second oxidation state, wherein the first oxidation state is different from the second oxidation state; co-feeding the first chemical substrate and the second chemical substrate at a predetermined mixture ratio to the anaerobic organism; co-utilizing, by the anaerobic organism, the first chemical substrate and the second chemical substrate to produce a chemical; and controlling a regeneration of reduced electron carriers in cells of the anaerobic organism caused by a metabolism of the co-utilization of the first chemical substrate and the second chemical substrate. The anaerobic organism may comprise a fermentative organism. The first chemical substrate may comprise any of galacturonate and galacturonate polymers. The second chemical substrate may comprise a carbohydrate. The carbohydrate may comprise any of glucose, mannose, galactose, fructose, arabinose, xylose, sucrose, lactose, maltose, cellobiose, and starch. The controlling of the amount of reduced electron carriers may comprise altering the predetermined mixture ratio of the first chemical substrate to the second chemical substrate. The reduced electron carriers may comprise any of NADH, NADPH, thiredoxins, and ferrodoxins.

Another embodiment provides a method of controlling a fermentation process, the method comprising providing a fermentative organism; co-feeding the fermentative organism with a mixture of at least two feedstock materials; and controlling a fermentation process of the fermentative organism based on a ratio of the at least two feedstock materials. The fermentative organism may co-utilize the at least two feedstock materials in the fermentation process simultaneously. The fermentative organism may co-utilize the at least two feedstock materials from an onset of fermentation until one of the at least two feedstock materials is depleted. The fermentation process may co-utilize the at least two feedstock materials in an oxidized or reduced form. The fermentation process may produce any of acetate and butyrate.

These and other aspects of the embodiments herein will be better appreciated and understood when considered in conjunction with the following description and the accompanying drawings. It should be understood, however, that the following descriptions, while indicating exemplary embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIGS. 7A through 7I are graphical illustrations depicting the resulting experimental production of various chemicals by co-feeding different feedstock materials to different types of fermentative cells.

DETAILED DESCRIPTION

Figure 1:
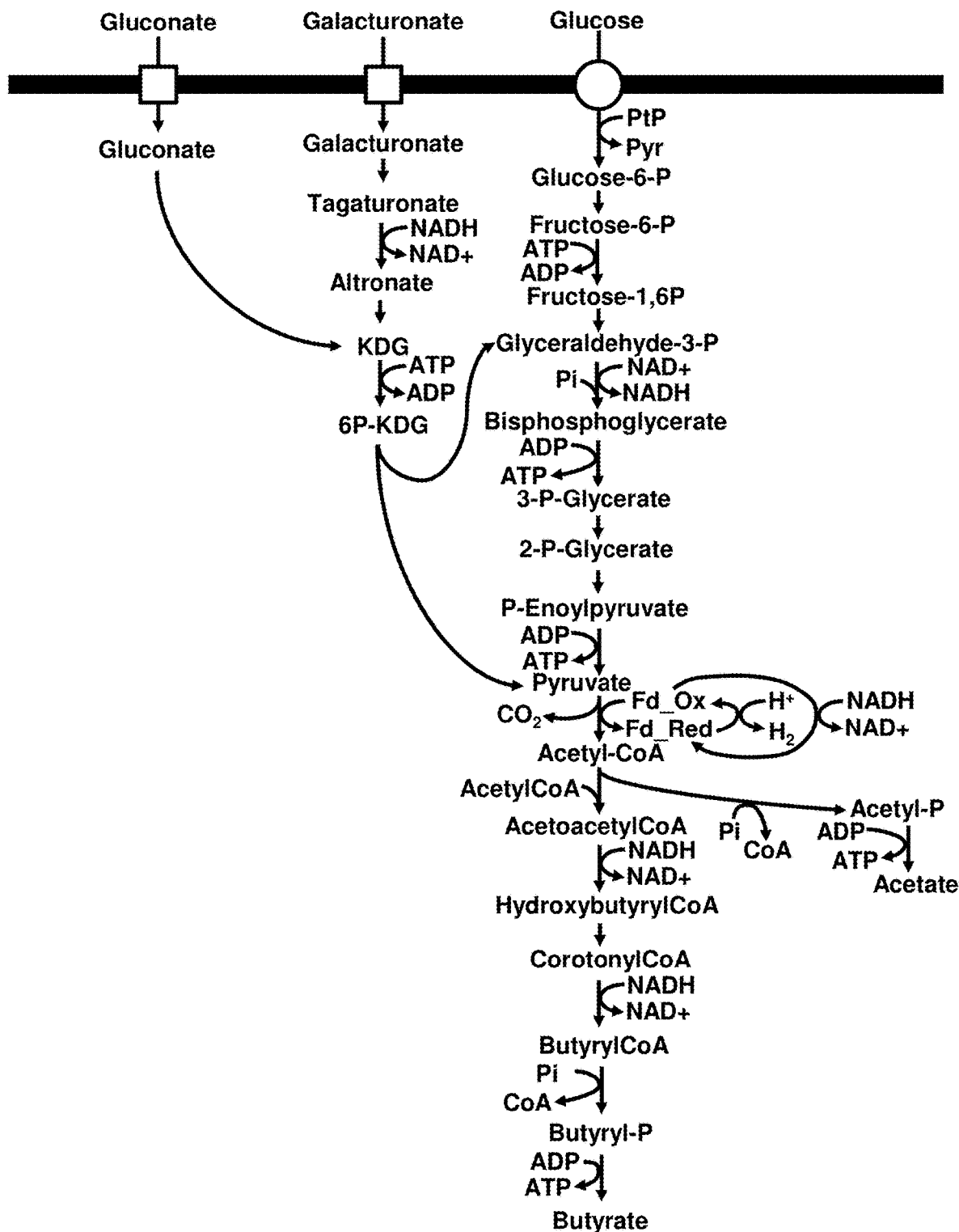
FIG. 1 illustrates the metabolic pathway of gluconate, galacturonate, and glucose inside the *Clostridium acetobutylicum* bacterial cell.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide a methodology that allows for fine-tuning of metabolic state/output of desired products, which overcomes the limitations of the conventional strategies of metabolic engineering and bioinformatics. The methodology includes co-feeding of any of galacturonate and galacturonate polymers with carbohydrates to fine tune the metabolic state of anaerobic organisms via controlled regeneration of reduced electron carriers for (i) chemical production using organisms with natural or synthetic pathways, (ii) inhibition of side-product formation during chemical production with organisms containing natural and/or synthetic pathways The embodiments herein control metabolism for optimized biological and chemical production and the modulation of microbial communities for increased performance of organisms and materials. Referring now to the drawings, and more particularly to FIGS. 1 through 7I, where similar reference characters denote corresponding features consistently throughout the figures, there are shown preferred embodiments.

"Microorganism" as used herein refers to unicellular or multicellular organisms, includes bacteria, archaea, protists, protozoans, or eukaryotes.

"Anaerobic organism" as used herein refers to any organism that can metabolize and grow without the presence of oxygen, organism may be unicellular or multicellular organism.

"Feedstock" and "Substrate" may be used interchangeably and is defined as material comprising carbohydrates, uronic acids, aldonic acids, and others.

"Effective amount" is used herein to denote a quantity or concentration of the substrate known to be effective to achieve the desired and known result of the substrate. The actual amount contained in the molecular complex or composition, likely will vary since some of the substrate composition may not completely penetrate the microorganism all together. Using the guidelines provided herein, those skilled in the art are capable of determining the acceptable amount of substrate described herein, and to use the requisite amount. For example, a suitable dosage adjustment may be made by the attending physician or veterinarian depending upon the age, sex, weight and general health of the subject. Such a composition may be administered parenterally, optionally intramuscularly or subcutaneously. However, the composition may also be formulated to be administered by any other suitable route, including orally or topically.

The use of substrates of different oxidation states by organisms results in different levels of reduced intracellular electron carrying cofactors. The embodiments herein use the finding showing co-utilization of galacturonate and/or glucose by *Clostridium acetobutylicum*, which is counterintuitive since glucose was conventionally thought to be the preferred substrate. The embodiments herein use ratios of oxidized and reduced substrates that cells can co-utilize to control the intracellular redox environment via controlled production of reduced cofactors. This allows for fine-tuned control of the metabolic state of the organisms as opposed to simple switching of the substrate oxidation state, which results in stepwise control.

The embodiments herein provide for the co-utilization of any of galacturonate and galacturonate polymers with glucose without genetic modification (through the introduction of a pathway or deletion/modification of natural genes). As described above, for many organisms including *Clostridium acetobutylicum*, it was conventionally thought that glucose is the preferred substrate and in the presence of glucose, the use of other substrates by the cells would be inhibited. The embodiments herein demonstrate that without genetic modification, cells co-utilize any of galacturonate and galacturonate polymers together with glucose, and that this co-utilization can be used to fine-tune the redox environment in the cells.

When fermentative organisms such as *Clostridium acetobutylicum* cells are grown on different oxidized substrates, the metabolic state of the cells may be shifted to different outputs. For example, when grown solely on galacturonate, a more oxidized substrate compared to glucose, the metabolism is shifted predominantly towards acetate production, which is a more oxidized product of two major products. When grown solely on glucose, less acetate is produced in comparison with butyrate, which is a more reduced product. This happens because the cells try to adjust their metabolite state by altering production of reduced electron carriers such as NADH and/or NADPH. FIG. 1 is the metabolic pathway in *Clostridium acetobutylicum* that shows that more reduced electron carriers are produced during conversion of glucose to Acetyl-CoA, an intermediate product, than is needed to convert galacturonate in the same reaction.

Using an equal proportion mixture of these two substrates—glucose and galacturonate (or it's polymers)—indicates that co-utilization of both substrates occurs from the onset of fermentation until one of the substrates is depleted. Accordingly, the embodiments herein provide a technique to fine-tune the outputs of the two major fermentation products; acetate and butyrate, by co-feeding *Clostridium acetobutylicum* cells with different ratio mixtures (i.e., in terms of molar concentration) of these substrates.

FIG. 2A, with reference to FIG. 1, is a flow diagram illustrating a method 100 of generating chemicals, the method comprising providing (101) fermentative cells; co-feeding (103) any of galacturonate and galacturonate polymers with carbohydrates to the fermentative cells; and producing (105) a chemical from the fermentative cells. In an example, the fermentative cells may comprise any of *Clostridium acetobutylicum* and *Clostridium saccharoperbutylacetonicum* or another type of fermentative anaerobic organism. The alpha-D and beta-D form of galacturonate are generally stable in the solid form but when either is put in solution, they rapidly equilibrate. Thus, either the alpha-D or beta-D form of galacturonate may be used in accordance with the embodiments herein. A galacturonate polymer is generally a substance made up of repeated units of the same molecular structure (i.e., galacturonate). For example, pectin is a polymer of galacturonate. According to an example, the carbohydrates may comprise any of glucose, mannose, galactose, fructose, arabinose, xylose, sucrose, lactose, maltose, cellobiose, and starch. FIG. 2B, with reference to FIGS. 1 and 2A, indicates that the method 100 may comprise providing (107) a substantially equal proportion (i.e., in terms of molar concentration) of the any of galacturonate and galacturonate polymers and the carbohydrates for co-feeding to the fermentative cells.

Figure 2:
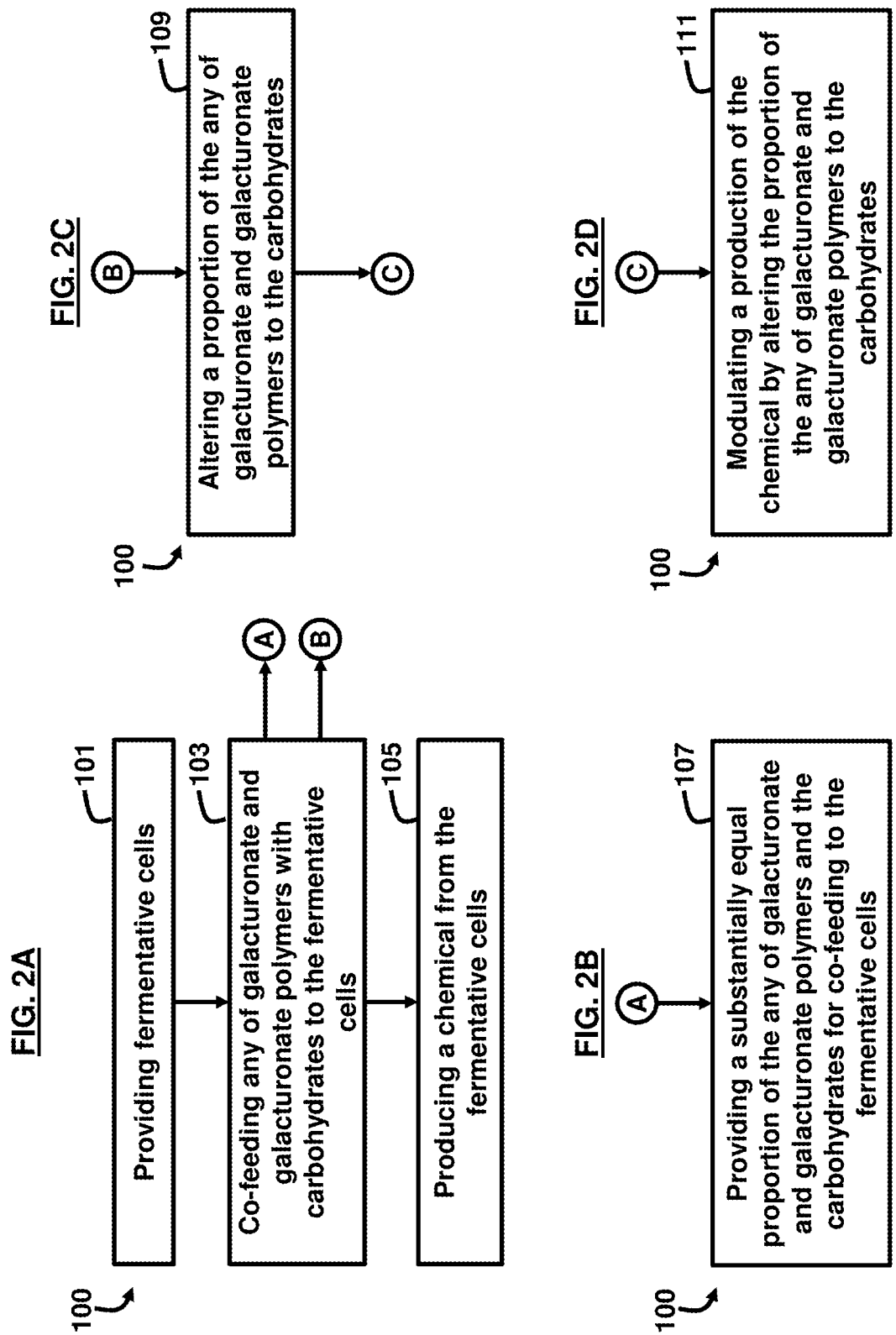
FIG. 2A is a flow diagram illustrating a method of producing chemicals from fermentative cells.
FIG. 2B is a flow diagram illustrating a method of co-feeding the fermentative cells for controlled chemical output.
FIG. 2C is a flow diagram illustrating a method of producing desired chemicals.
FIG. 2D is a flow diagram illustrating a method of controlling production of chemicals.

FIG. 2C, with reference to FIGS. 1 through 2B, indicates that the method 100 may comprise altering (109) a proportion (i.e., in terms of molar concentration) of the any of galacturonate and galacturonate polymers to the carbohydrates. FIG. 2D, with reference to FIGS. 1 through 2C, indicates that the method 100 may comprise modulating (111) a production of the chemical by altering the proportion of the any of galacturonate and galacturonate polymers to the carbohydrates. In an example, the chemical may comprise acetate. In another example, the chemical may comprise butyrate.

The method may comprise administering the feedstock mixture. The feedstock mixture may comprise an aqueous solution or a solid form. The method may comprise decontaminating the microorganism. The method may comprise administering the feedstock to the fermentation organism.

Experimentally, mixtures of any of galacturonate and galacturonate polymers with glucose are fed to *Clostridium acetobutylicum*. It was observed that the organism co-utilized the substrates. When grown on glucose, the organism produced approximately 10.7 mM of acetate and approximately 14.2 mM of butyrate. When grown on galacturonate, the organism produced approximately 23.6 mM of acetate and approximately 0.6 mM of butyrate. It was observed that an equal proportion mixture of galacturonate (or it's polymers) and glucose produced intermediate amounts of acetate and butyrate, approximately 18.5 mM and approximately 7.3 mM, respectively. Acetate is more oxidized than butyrate so by altering the feedstock, the production can be modulated between the two different molecules.

The embodiments herein provide a technique to modulate the availability of redox cofactors by feeding mixtures of substrates with different oxidation states. In organisms where the pathways for using the two substrates are native and the organisms co-utilize the substrates, the methodology provided by the embodiments herein can be used to control production levels of reduced cofactors without genetic engineering. This saves time and resources in the genetic engineering process, and provides a way to closely match reduced cofactor requirements, which allows for fine tuning of the process during scale-up. Accordingly, the ability to optimize production of reduced cofactors can increase yields of desired chemicals. Furthermore, the process provided by the embodiments herein may be used to modulate metabolism to reduce the production of undesirable side-products.

Figure 3:
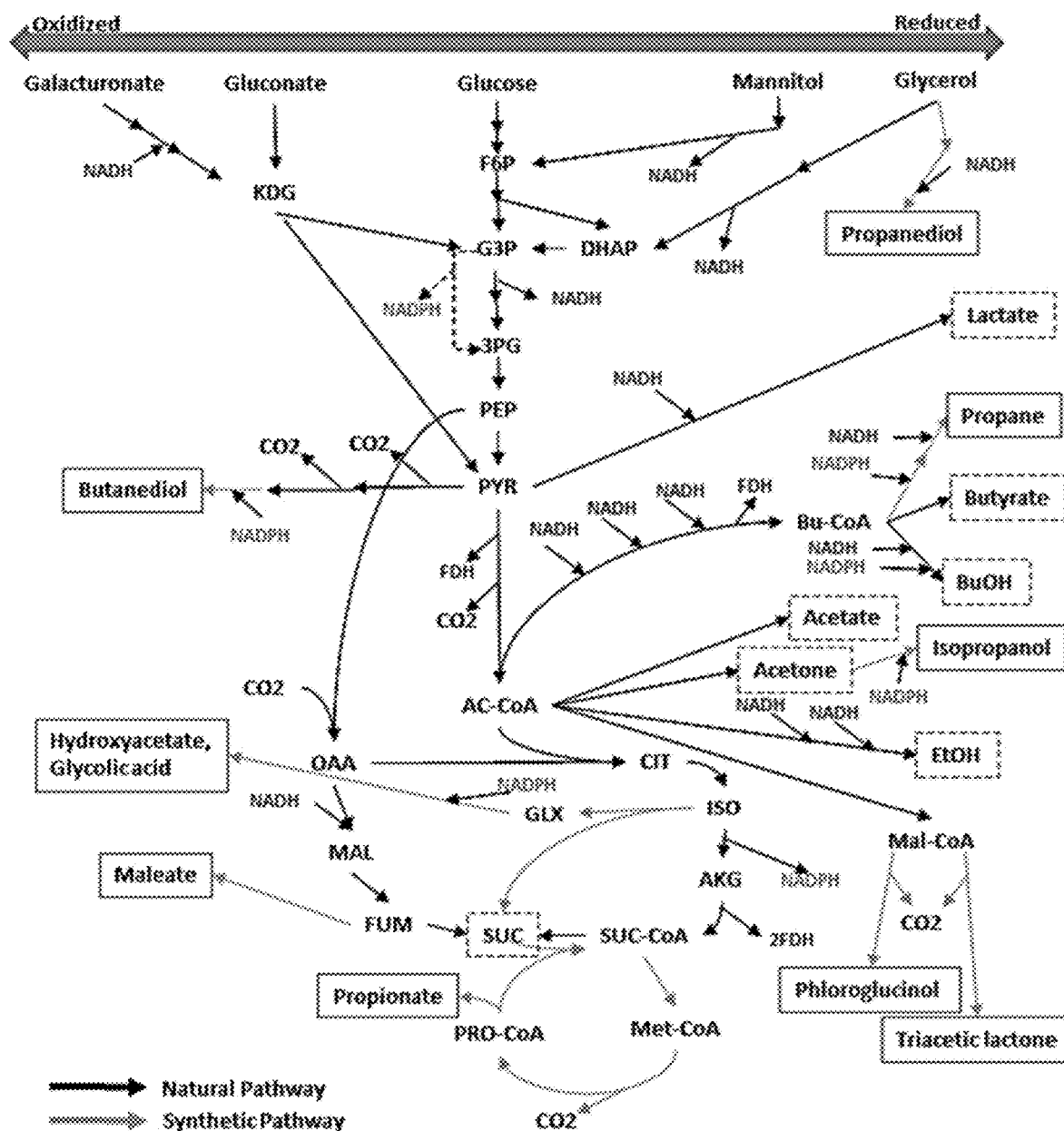
FIG. 3 illustrates various natural and synthetic pathway mapping sequences for producing different types of chemicals using *Clostridium* as a fermentative cell-line.

FIG. 3, with reference to FIGS. 1 through 2C, illustrates various natural and synthetic pathway mapping sequences within *Clostridium*, for producing different types of solvents. The growth of an anaerobic organism, such as *Clostridium acetobutylicum*, on substrates of different oxidation states, uses different metabolic pathways and different net energetics. *Clostridium acetobutylicum* may use carbon catabolite repression (CCR) to preferentially consume/uptake sugar/feedstock/substrate. By varying the mixed feedstock input, continuous net reductant and energetics can be mined, instead of discrete net energetics, thereby allowing for better control of a desired product. As shown in FIG. 3, various pathways are mapped based on various feedstock such as galacturonate, gluconate, glucose, mannitol, and glycerol. Tables 1 and 2 below provide the net moles that are derived.

TABLE 1

Net NADH/Reduced Ferredoxin/ATP per acetyl-CoA formed

| | Galacturonate | Gluconate | Glucose | Mannitol | Glycerol |
|---|---|---|---|---|---|
| NADH | 0 | 0.5 | 1 | 1.5 | 2 |
| Fd_red | 1 | 1 | 1 | 1 | 1 |
| ATP | 0.33 | 0.33 | 1 | 1 | 1 |

TABLE 2

Net NADH/Reduced Ferredoxin/ATP per acetyl-CoA used in product

| | Acetate | Isopropanol | Butyrate | EtOH | BuOH | Propane |
|---|---|---|---|---|---|---|
| NADH | 0 | −0.5 | −1.5 | −2 | −2.5 | −2.5 |
| Fd_red | 0 | 0 | 0.5 | 0 | 0.5 | 0.5 |
| ATP | 1 | 0 | 0.5 | 0 | 0 | 0 |

Transcriptomics, metabolomics, and proteomics studies can be performed on cultures grown on different feedstocks, to identify pathway activation and carbon flow during growth. The net energetics for growth on individual sugars are well understood. Identifying how bacteria metabolizes mixed sugars provides information to create continuous models of net energetics.

Figure 4:
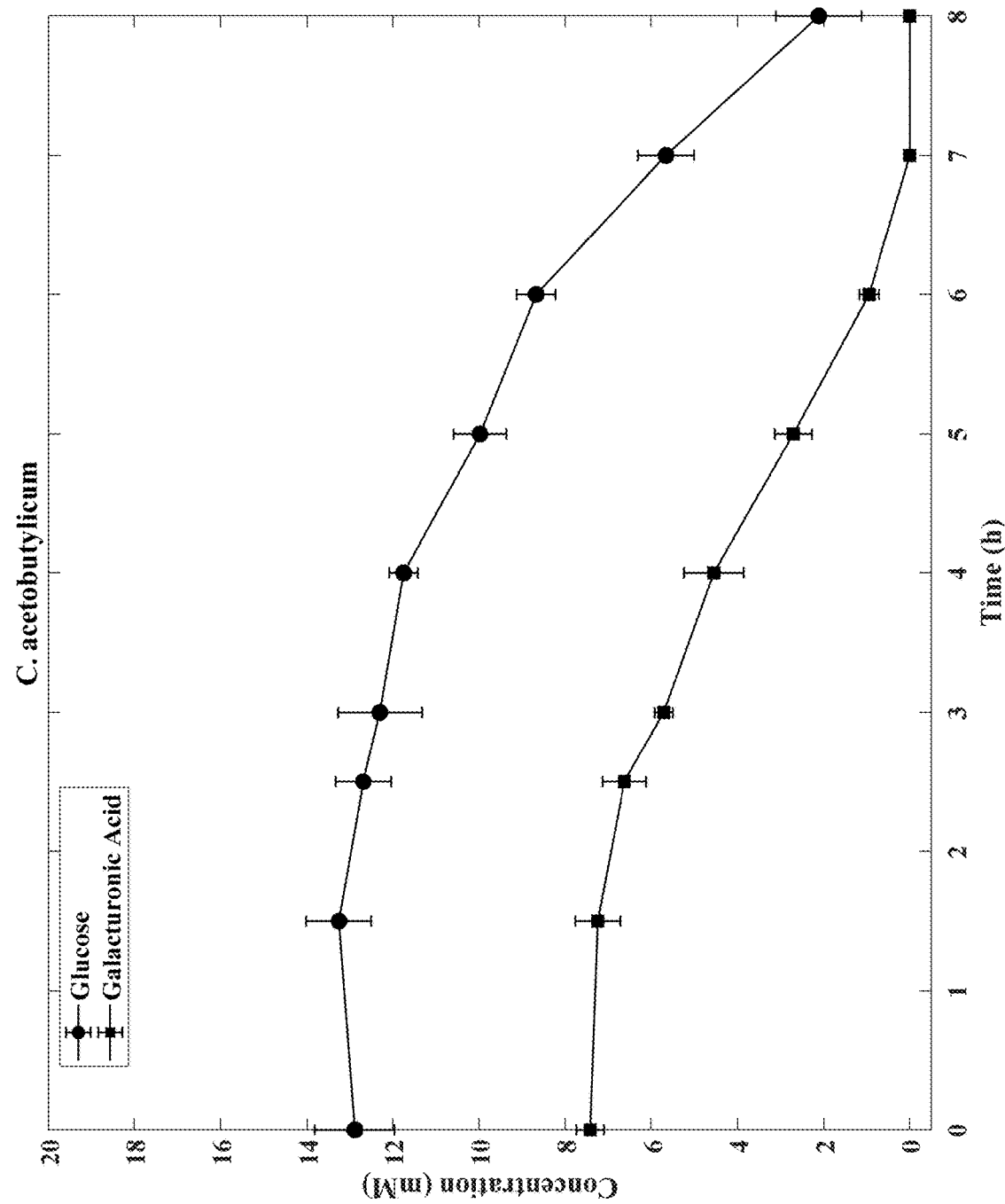
FIG. 4 is a graph illustrating the uptake of individual oxidized sugars mixed for co-feeding during a fermentation process of Clostridia *acetobutylicum;*

FIG. 4, with reference to FIGS. 1 through 3, is a graph illustrating the concentration of various feedstock during a fermentation process. The graph shows the co-utilization of glucose and galacturonate in *Clostridium acetobutylicum* fermentation. The co-utilization of any of galacturonate and galacturonate polymers with glucose could be used to control the metabolic state of the cells by altering the production of reduced electron carriers such as NADH and/or NADPH.

This can allow for fine-tuning production of chemicals. The overall trend of the concentration over time shown in FIG. 4 for galacturonic (gal) acid and glucose (glu) is generally the same; i.e., a gradual decrease in the concentration over time. For example, the concentration of the galacturonic acid is approximately 7.5 at time 0 with a gradual decline in concentration to approximately 4 at approximately 3 hours, followed by a greater decline in concentration resulting in a 0 concentration at approximately 7 hours. The concentration of the glucose is approximately 13 at time 0 with an initial increase in concentration to approximately 14 at approximately 1.3 hours, followed by a gradual decline in concentration to approximately 12 at approximately 4 hours, followed by a greater decline in concentration to approximately 8.5 at approximately 6 hours, and followed by a much greater decline in concentration resulting in a concentration of approximately 2.5 at approximately 8 hours.

The embodiments herein provide a methodology to affect the amount of NADH and/or NADPH in a system, which provides an effective tool for metabolite output fine-tuning. The embodiments herein achieve this by mixing different parts of these two oxidized substrates, and utilizing *Clostridium acetobutylicum*'s ability to co-utilize these two substrates, which are present in a wide variety of feedstocks, in order to fine tune product output. Cells can co-utilize galacturonate and/or glucose, which is not intuitive, and thus contrary to conventional thought, since glucose is thought to be the preferred substrate for many organisms. Moreover, when fed multiple substrates, cells tend to use the substrates sequentially based upon the organism's substrate preference.

Figure 5:
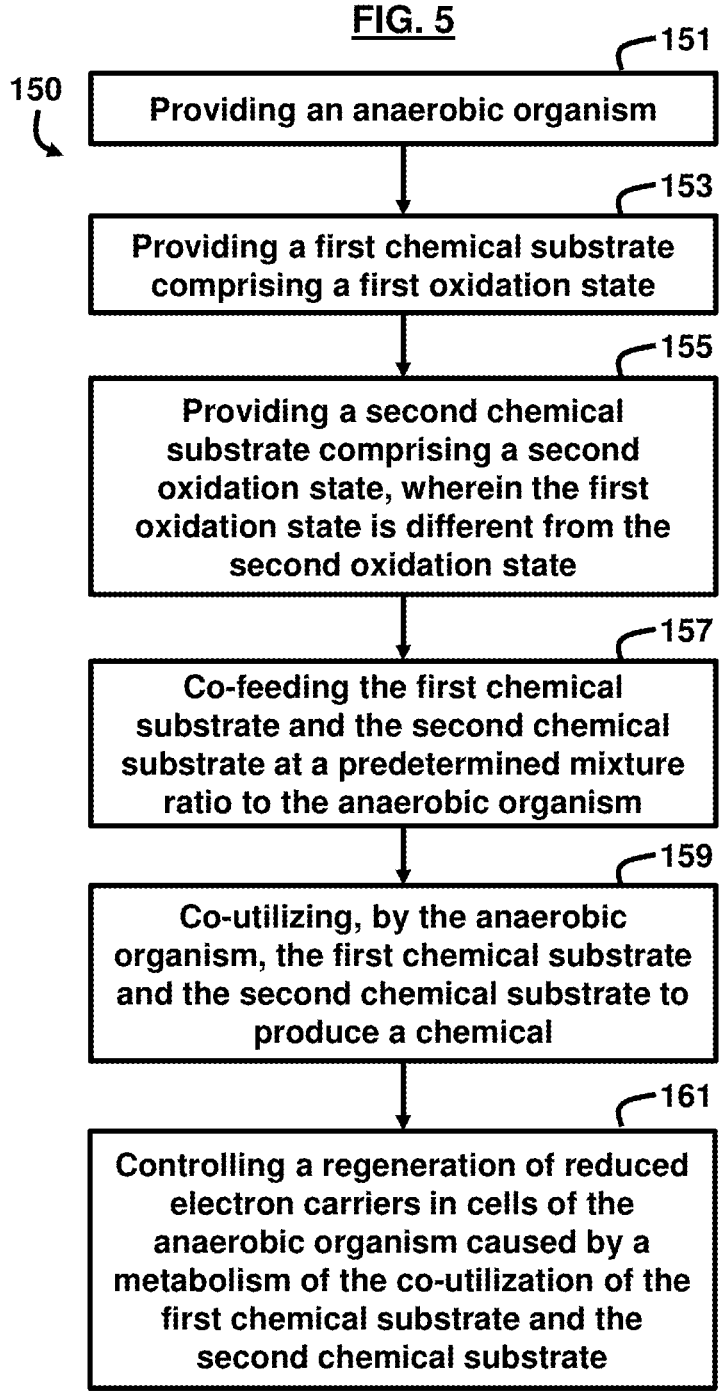
FIG. 5 is a flow diagram illustrating a method of controlling a metabolic process.

FIG. 5, with reference to FIGS. 1 through 4, is a flow diagram illustrating a method 150 of controlling a metabolic process. The method 150 comprises providing (151) an anaerobic organism; providing (153) a first chemical substrate comprising a first oxidation state; providing (155) a second chemical substrate comprising a second oxidation state, wherein the first oxidation state is different from the second oxidation state; co-feeding (157) the first chemical substrate and the second chemical substrate at a predetermined mixture ratio (i.e., in terms of molar concentration) to the anaerobic organism; co-utilizing (159), by the anaerobic organism, the first chemical substrate and the second chemical substrate to produce a chemical; and controlling (161) a regeneration of reduced electron carriers in cells of the anaerobic organism caused by a metabolism of the co-utilization of the first chemical substrate and the second chemical substrate. In an example, the anaerobic organism may comprise a fermentative organism. The first chemical substrate may comprise any of galacturonate and galacturonate polymers, and the second chemical substrate may comprise a carbohydrate. According to an example, the carbohydrate may comprise glucose, mannose, galactose, fructose, arabinose, xylose, sucrose, lactose, maltose, cellobiose, and starch. The controlling of the amount of reduced electron carriers may comprise altering the predetermined mixture ratio (i.e., in terms of molar concentration) of the first chemical substrate to the second chemical substrate. For example, the reduced electron carriers may comprise any of NADH, NADPH, thiredoxins, and ferrodoxins.

Figure 6:
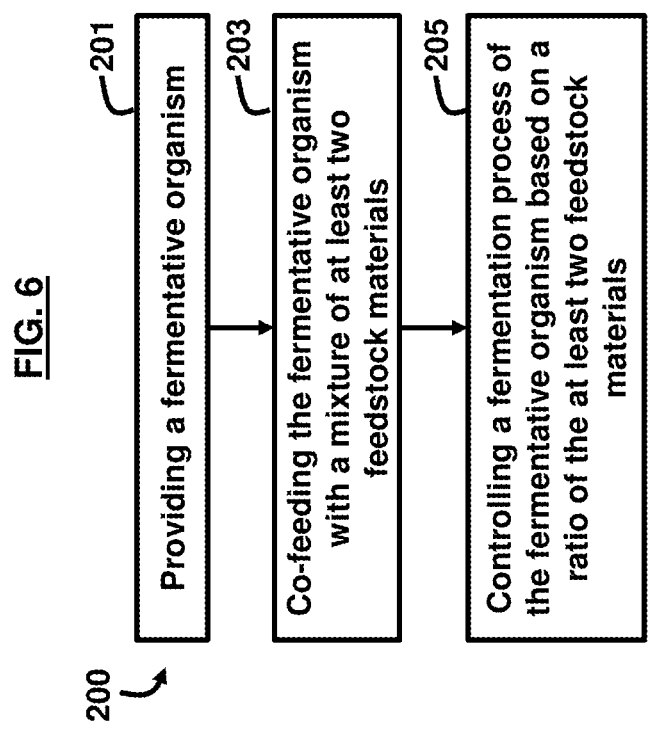
FIG. 6 is a flow diagram illustrating a method of controlling a fermentation process.

FIG. 6, with reference to FIGS. 1 through 5, is a flow diagram illustrating a method 200 of controlling a fermentation process. The method 200 comprises providing (201) a fermentative organism; co-feeding (203) the fermentative organism with a mixture of at least two feedstock materials; and controlling (205) a fermentation process of the fermentative organism based on a ratio (i.e., in terms of molar concentration) of the at least two feedstock materials. The fermentative organism may co-utilize the at least two feedstock materials in the fermentation process simultaneously based upon a metabolic preference of the fermentative organism. The fermentative organism may co-utilize the at least two feedstock materials from an onset of fermentation until one of the at least two feedstock materials is depleted. The fermentation process may co-utilize the at least two feedstock materials in an oxidized or reduced form. The fermentation process may produce any of acetate and butyrate.

The feedstock mixture may be administered as a supplement during fermentation. The feedstock mixture may comprise an aqueous solution or a solid form. The feedstock may be administered by intravenous injection, subcutaneous injection, or intraperitoneal injection.

In one embodiment, the feedstock mixture may be an aqueous solution or solid form. Thus, for example it may be in tablet, coated tablet, delayed or sustained release coated tablet, capsule, suppository, pessary, gel, emulsion, syrup, dispersion, suspension, emulsion, powder, cream, paste, etc. In another embodiment, the feedstock mixture may be administered as a supplement, such as in a chaser in a shake or drink form.

In one embodiment, the feedstock mixture may be administered with two or more different therapeutic compounds. Two different substrates may be administered either in the same formulation or in a separate formulation, either concomitantly or sequentially.

The composition of the embodiments herein may be administered to the production organism. For example, the composition may be administered by, but not limited to, oral and non-oral preparations (e.g., intramuscular, subcutaneous, transdermal, visceral, IV (intravenous), IP (intraperitoneal), intraarticular, placement in the ear, ICV (intracerebralventricular), intraarterial, intrathecal, intracapsular, intraorbital, injectable, pulmonary, nasal, rectal, and uterine-transmucosal preparations).

In some embodiments, a process of decontaminating the surface occurs by applying the feedstock or substrate to a surface that includes one or more microbes. Any delivery mechanism for decontaminating a surface may be used including spraying, immersing, or other contact mechanism.

In another embodiment, the different components of the substrate mixture may be packaged together in separate containers. If appropriate, and mixed immediately before use, such packaging of the components separately may permit long-term storage without losing the active component's function. Sterilization may be preceded or followed by packing into containers. If desired, the composition of the embodiments herein may contain pharmaceutically acceptable additives, such as dissolving aids, buffering components, stabilizers, and the like. The substrates may be supplied in containers of any sort such that the life of the different components are preserved and are not adsorbed or altered by the materials of the container. For example, sealed glass ampules may contain lyophilized substrates and variants, derivatives and structural equivalents thereof, or buffers that have been packaged under a neutral, non-reacting gas, such as nitrogen. Other containers include test tubes, vials, flasks, bottles, syringes, or the like. Containers may have a sterile access port, such as a bottle having a stopper that may be pierced by a hypodermic injection needle. Other containers may have two compartments that are separated by a readily removable membrane that upon removal permits the components to be mixed. Removable membranes may be glass, plastic, rubber, etc.

Suitable pharmaceutically acceptable carriers facilitate administration of the substrate or feedstocks are physiologically inert and/or nonharmful. Carriers may be selected by one skilled in the art. Exemplary carriers include sterile water or saline, calcium phosphate, gelatin, dextran, agar, pectin, peanut oil, olive oil, sesame oil, and water. Additionally, the carrier or diluent may include a time delay material, such as glycerol monostearate or glycerol distearate alone or with a wax. In addition, slow release polymer formulations may be used.

The substrates or feedstock provided by the embodiments herein may additionally contain stabilizers such as thimerosal (ethyl(2-mercaptobenzoate-S)mercury sodium salt) (available from Sigma Chemical Company, St. Louis, Missouri), for example, or physiologically acceptable preservatives.

The composition provided by the embodiments herein may also contain conventional pharmaceutical ingredients, such as preservatives, or chemical stabilizers. Suitable ingredients operable herein include, for example, casamino acids, gelatin, phenol red, N—Z amine, monopotassium diphosphate, lactalbumin hydrolysate, and dried milk.

Bacterial culture conditions and strains have been previously published. All strains and cultures were maintained or grown in an atmosphere of 5.0% $H_2$, 5.0% $CO_2$, and 90.0% $N_2$. *Clostridium acetobutylicum* strain ATCC 824 was obtained from ATCC and cultured using company protocol at 37° C. into Clostridial growth medium or CGM containing 0.75 g $KH_2PO_4$, 0.75 g $K_2HPO_4$, 1.0 g NaCl, 0.017 g $MnSO_4.5H_2O$, 0.70 g $MgSO_4.7H_2O$, 0.01 g $FeSO_4.7H_2O$, 2.0 g l-asparagine, 5.0 g yeast extract, 2.0 g $(NH_4)_2SO_4$, and 0.5% final concentration of desired carbohydrate-D-glucose, D-galacturonic acid, D-gluconic acid—at pH 6.5. Active cultures from initial growth stock were added to potato glucose medium to be maintained and stored as a spore solution. Potato glucose medium or PGM contains per liter of $H_2O$—150 g grated fresh potato, 10 g D-glucose, 0.5 g $(NH_4)_2SO_4$, and 3 g $CaCO_3$. The medium was boiled for 1 hour and strained through gauze before sterilization and use for culture. Spore solution was activated for culturing through a heat shock at 80° C. for 9 minutes. Shocked spore solution was added to CGM containing the feed stock of choice and grown to late log of 0.8 at optical density of 600 nm ($OD_{600}$) at 37° C.

Another problem that the embodiments herein overcome is using oxidized feedstocks to increase the susceptibility of anaerobic organisms in complex settings. U.S. patent application Ser. No. 15/939,329, the complete disclosure of which, in its entirety, is herein incorporated by reference, describes the use of galacturonate to increase the susceptibility of anaerobic organisms to nitroimidazole antibiotics. In the presence of other substrates, the organisms may not utilize the galacturonate, which is required for increased antibiotic susceptibility. The embodiments herein provide a method demonstrating that co-feeding of any of galacturonate and galacturonate polymers with carbohydrates is possible to modulate the redox state of the cells. This further indicates that the method provided by the embodiments herein can allow for even greater fine-tuning of metabolism.

FIGS. 7A through 7I, with reference to FIGS. 1 through 6, illustrate various graphical time plots showing the experimental results of consumption of substrates by different *Clostridium* bacteria, indicating various chemicals that are produced when the bacteria are co-fed on two or more substrates. The percentages described below and in the figures are in terms of the molar concentrations of the respective substrates.

Figure 7B:
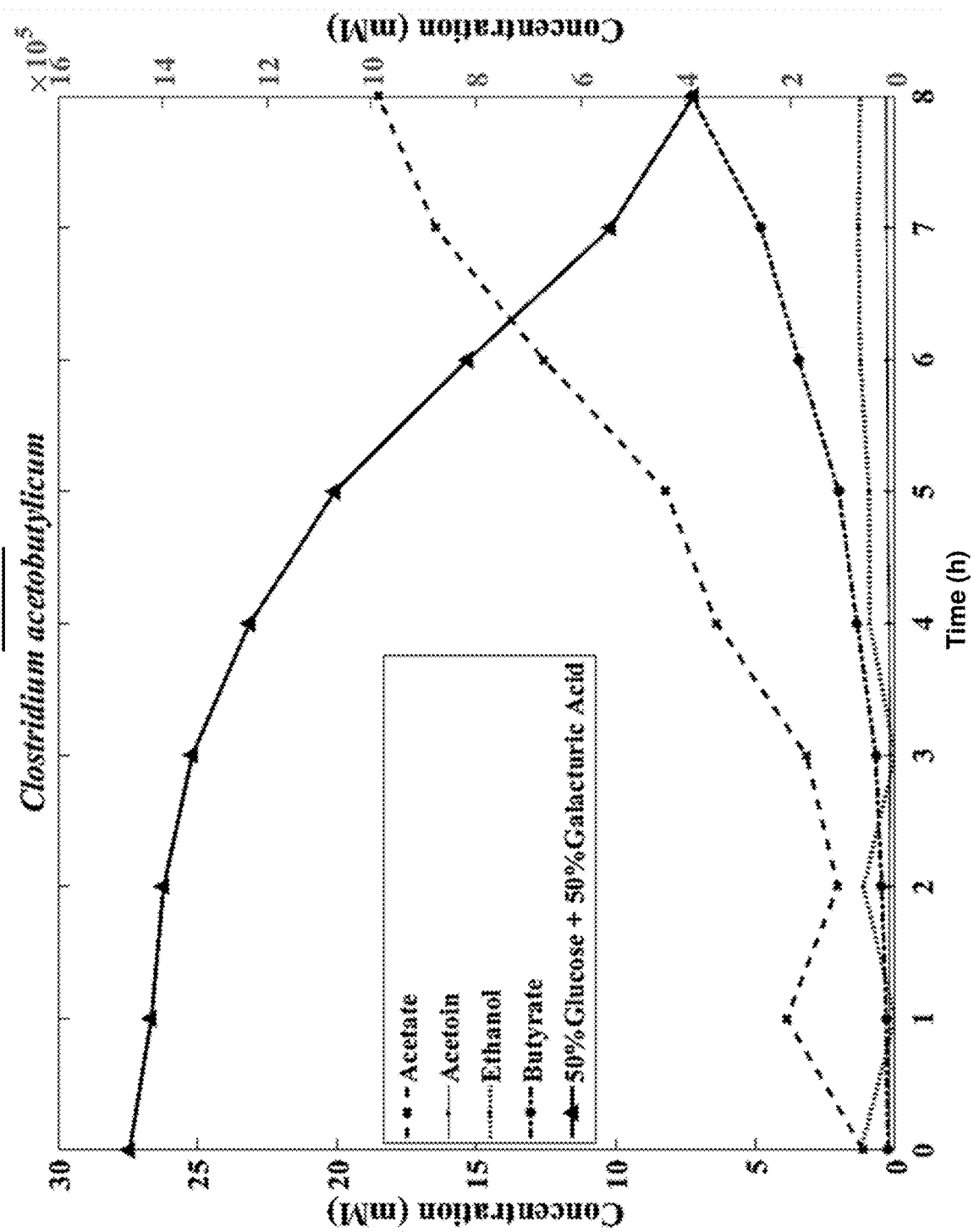
Figure 7C:
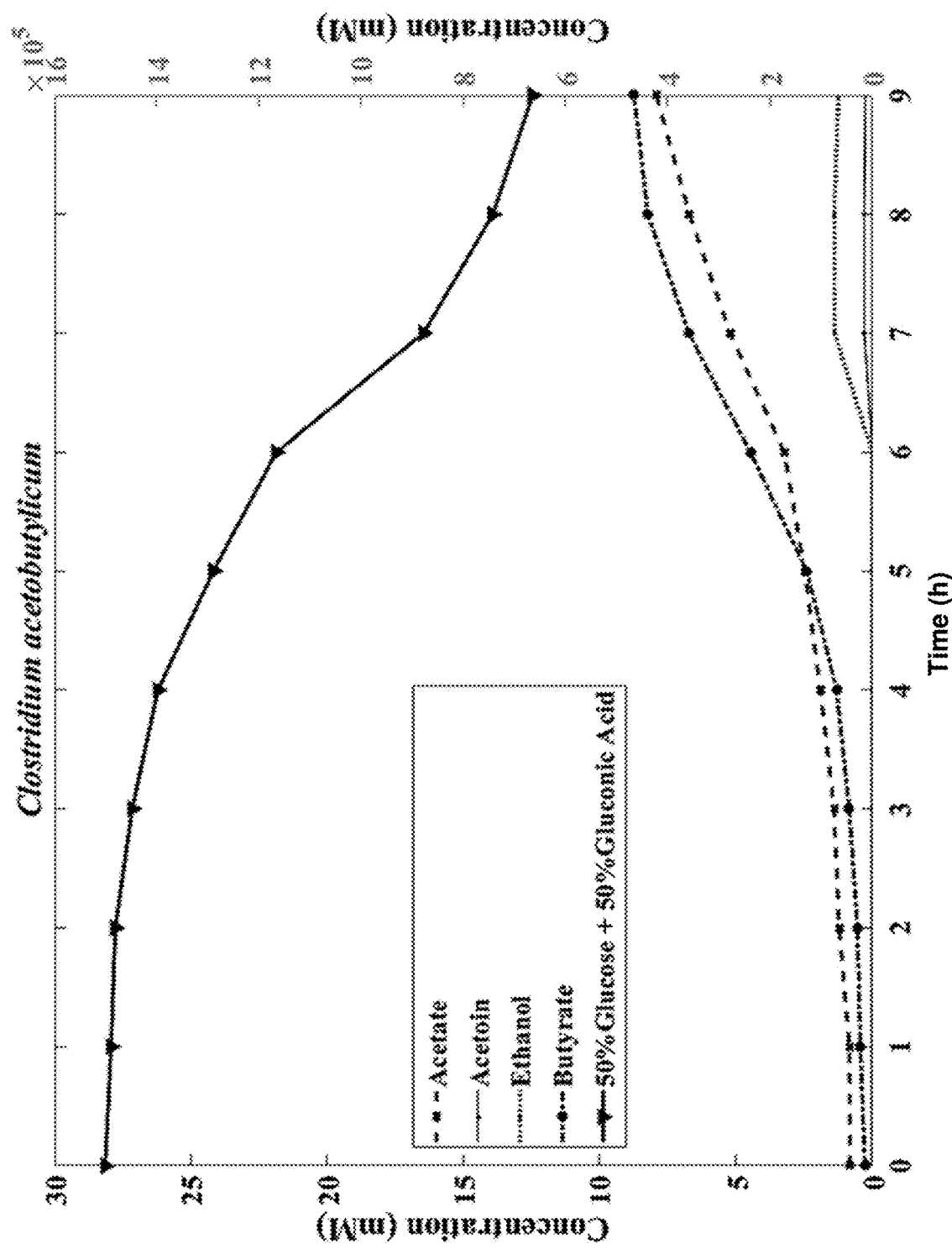
Figure 7E:
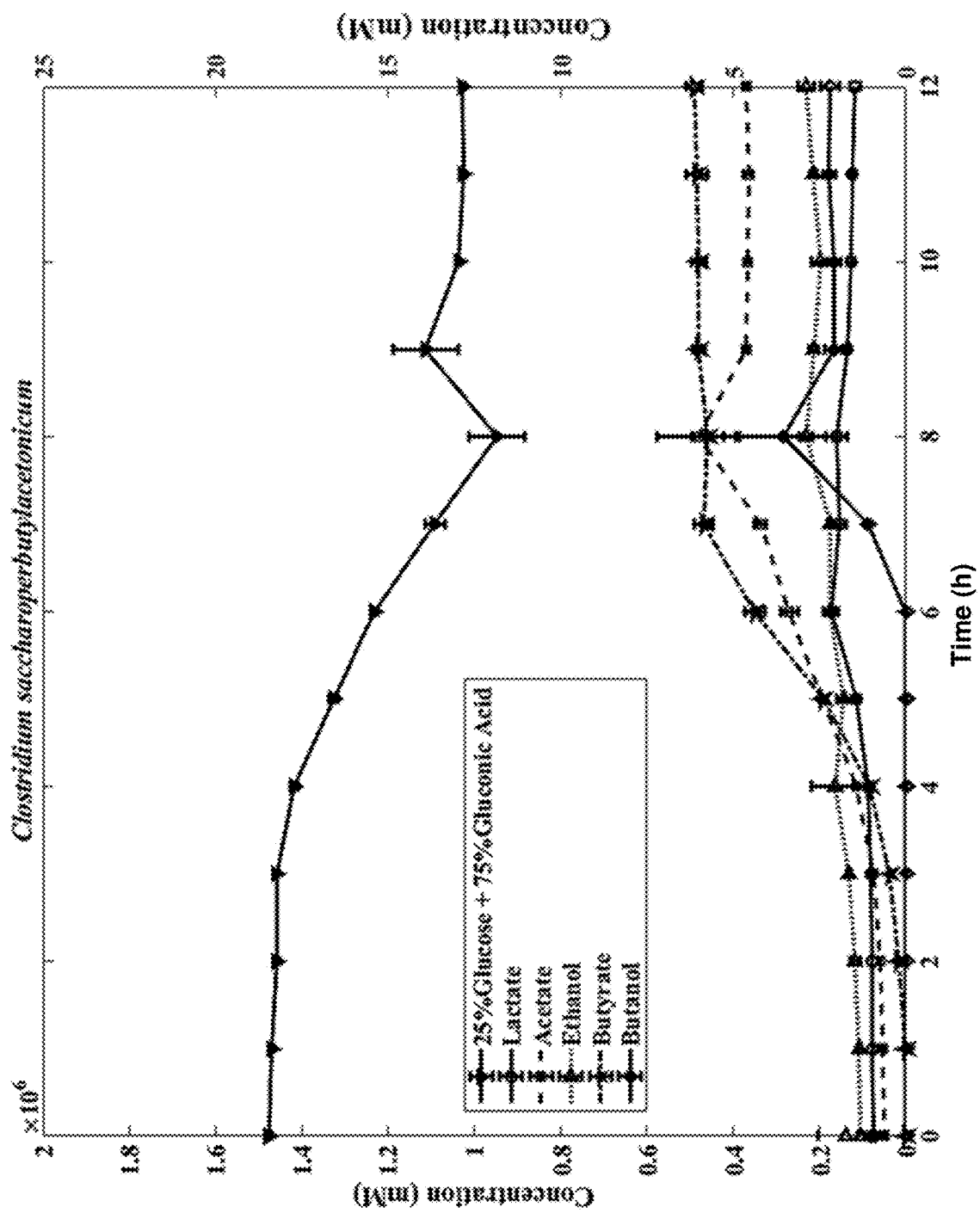
Figure 7F:
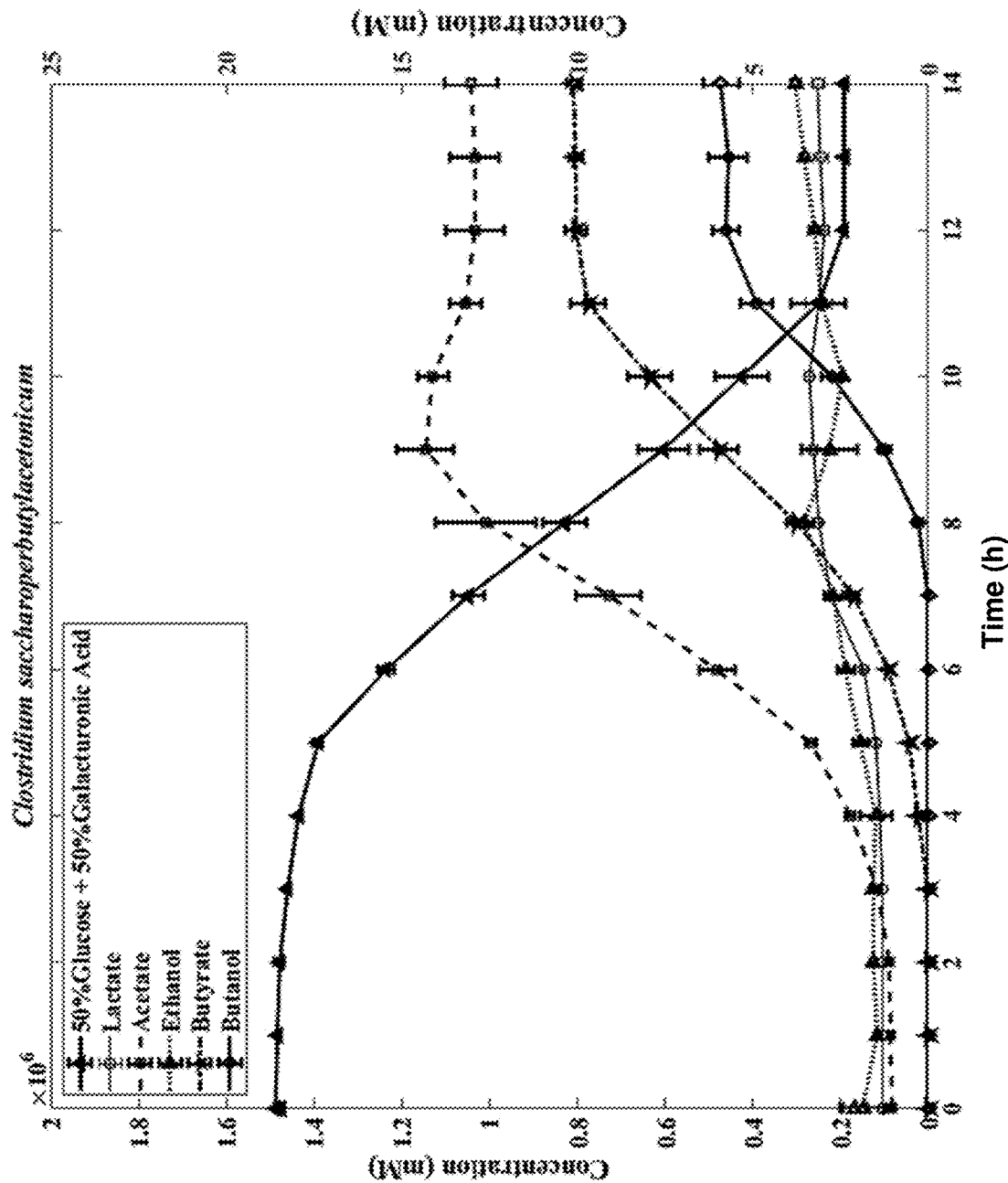
Figure 7G:
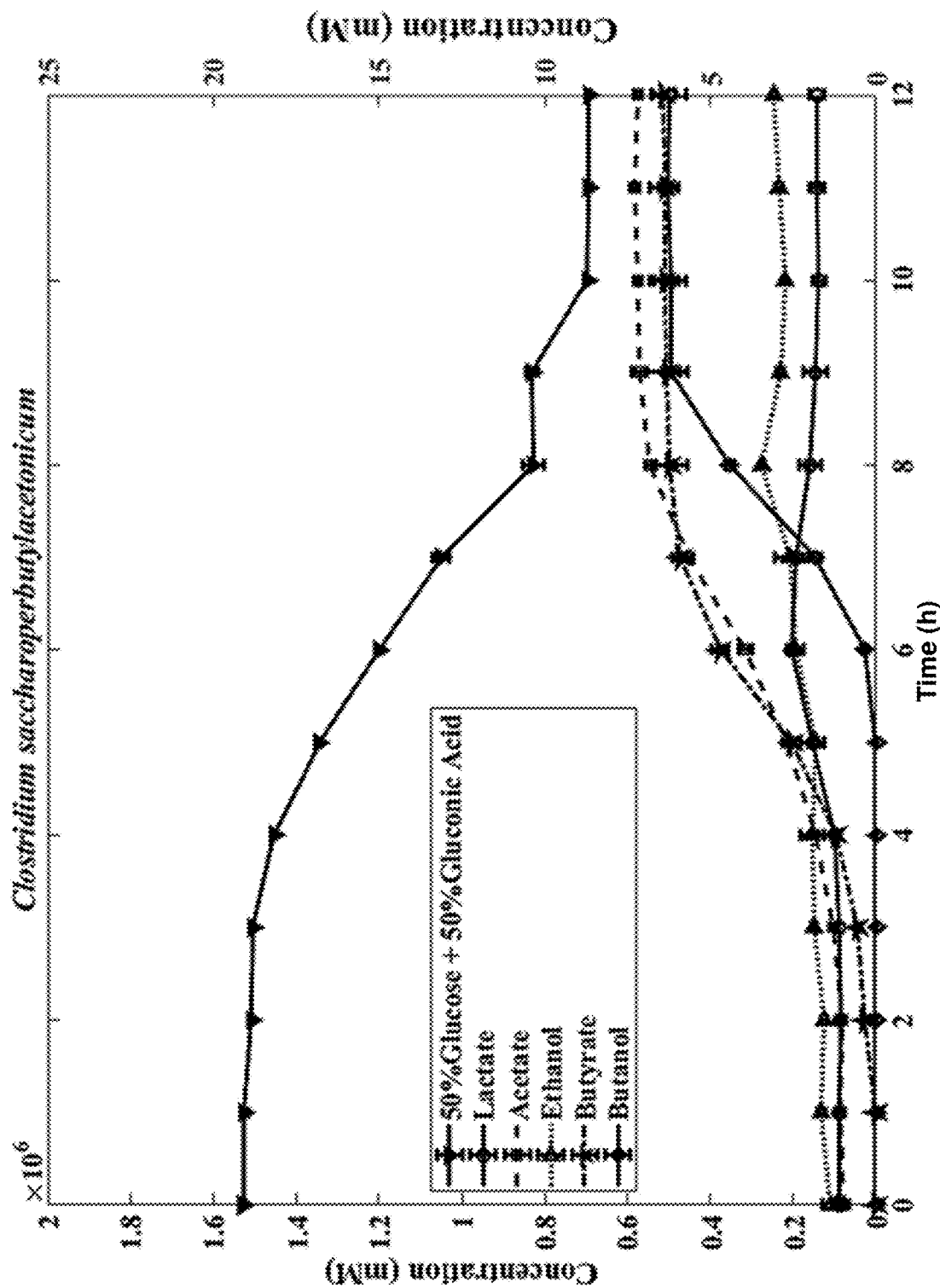
Figure 7H:
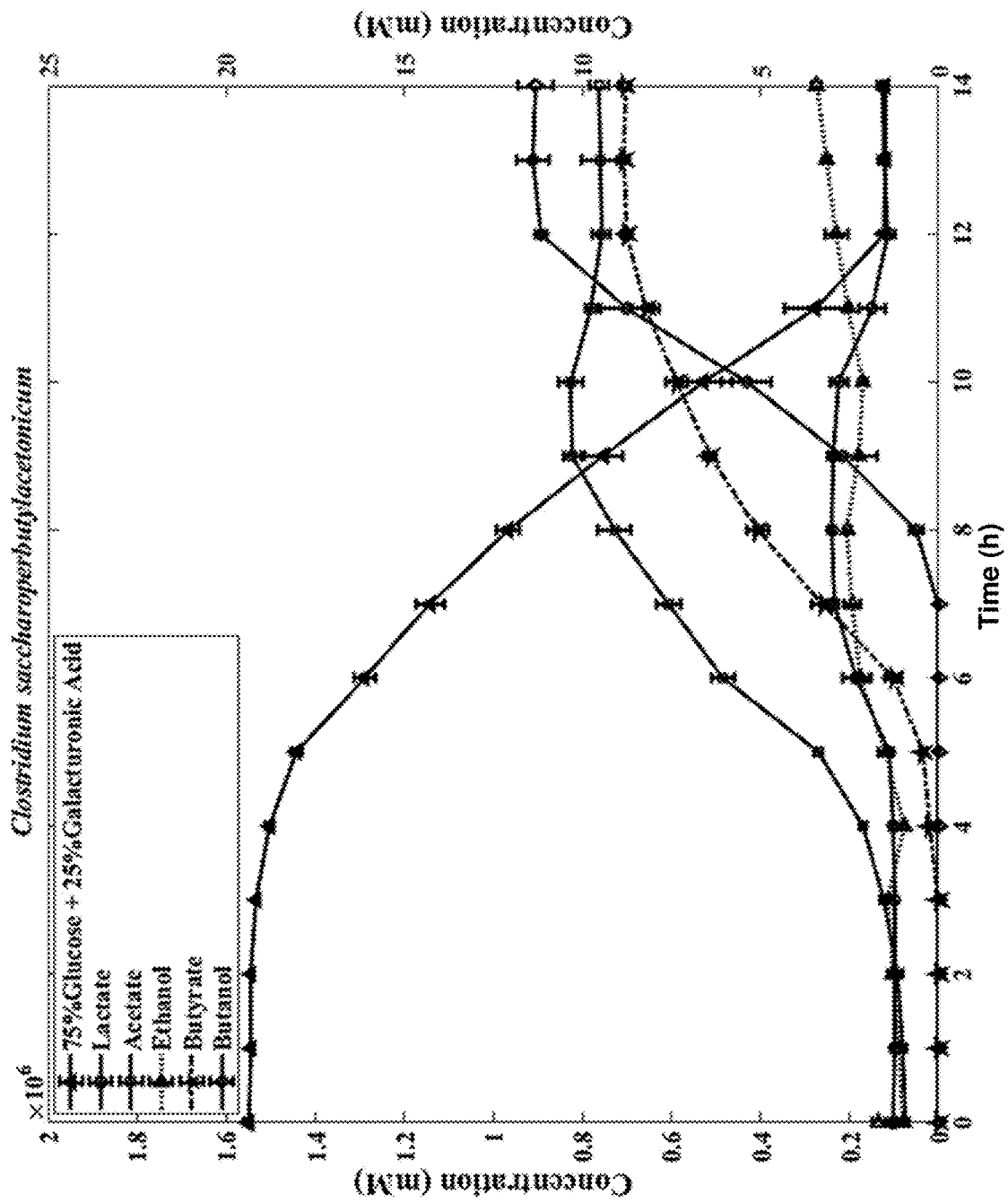
Figure 7I:
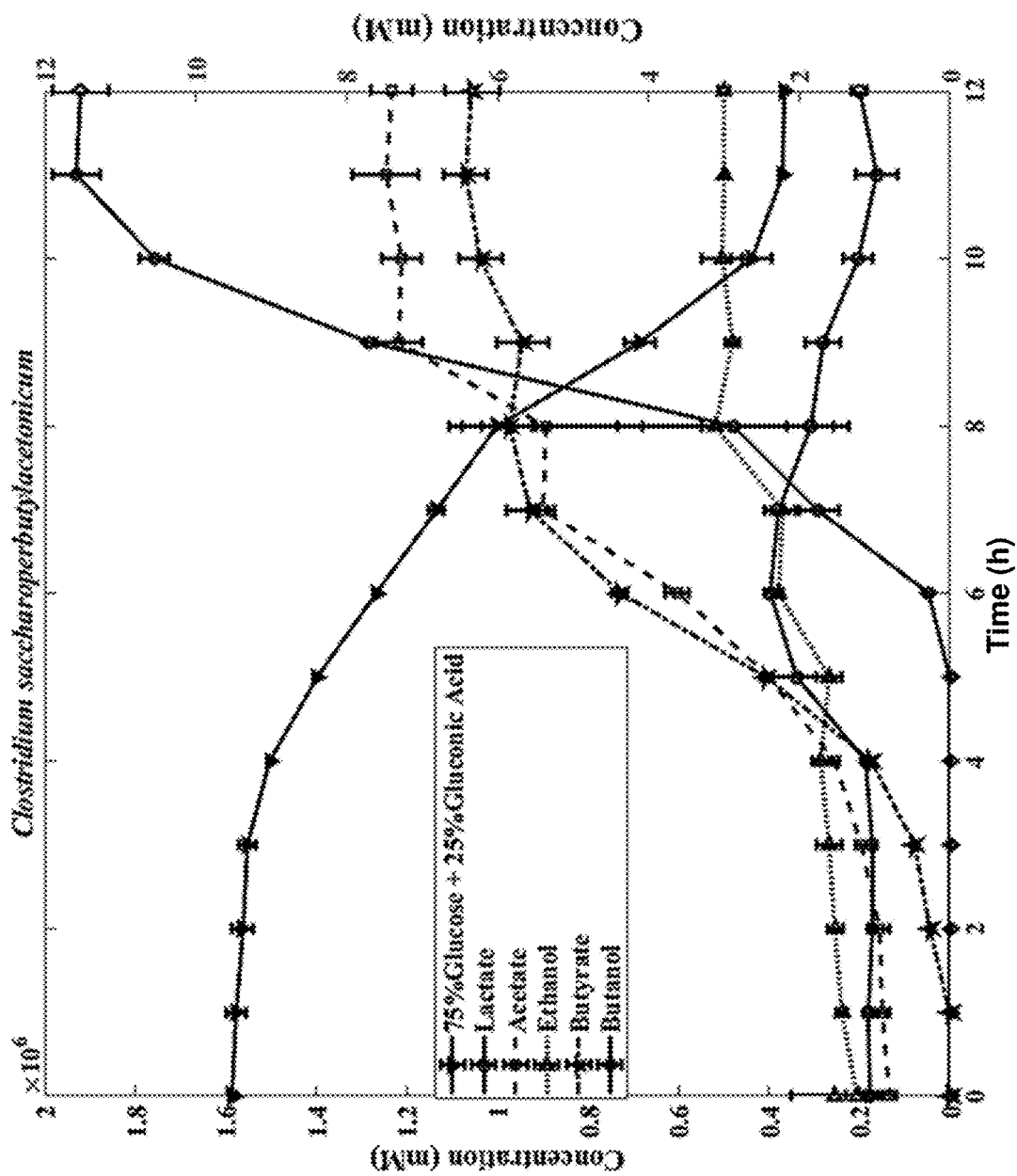

FIG. 7A illustrates the production of acetate, acetoin, ethanol, and butyrate when *Clostridium acetobutylicum* is co-fed 50% of galacturonic acid and 50% of gluconic acid. FIG. 7B illustrates the production of acetate, acetoin, ethanol, and butyrate when *Clostridium acetobutylicum* is co-fed 50% of glucose and 50% of galacturonic acid. FIG. 7C illustrates the production of acetate, acetoin, ethanol, and butyrate when *Clostridium acetobutylicum* is co-fed 50% of glucose and 50% of gluconic acid. FIG. 7D illustrates the production of lactate, acetate, ethanol, butyrate, and butanol when *Clostridium saccharoperbutylacetonicum* is co-fed 25% of glucose and 75% of galacturonic acid. FIG. 7E illustrates the production of lactate, acetate, ethanol, butyrate, and butanol when *Clostridium saccharoperbutylacetonicum* is co-fed 25% of glucose and 75% of gluconic acid. FIG. 7F illustrates the production of lactate, acetate, ethanol, butyrate, and butanol when *Clostridium saccharoperbutylacetonicum* is co-fed 50% of glucose and 50% of galacturonic acid. FIG. 7G illustrates the production of lactate, acetate, ethanol, butyrate, and butanol when *Clostridium saccharoperbutylacetonicum* is co-fed 50% of glucose and 50% of gluconic acid. FIG. 7H illustrates the production of lactate, acetate, ethanol, butyrate, and butanol when *Clostridium saccharoperbutylacetonicum* is co-fed 75% of glucose and 25% of galacturonic acid. FIG. 7I illustrates the production of lactate, acetate, ethanol, butyrate, and butanol when *Clostridium saccharoperbutylacetonicum* is co-fed 75% of glucose and 25% of gluconic acid. These results demonstrate the validity of producing various chemicals in suitable yields by co-feeding various concentrations of feedstock materials to fermentative cells.

The embodiments herein can be utilized in various applications. For example, the techniques provided by the embodiments herein may be used for the regulation of the availability of electron carrying cofactors for fine-tuning metabolite output through optimized production and decreased side-product formation, and can be used for production of biologically produced products including small molecules, therapeutics, bulk materials, and polymers. Additionally, the embodiments can provide for the regulation of the availability of electron carrying cofactors for the removal or neutralization of contaminants, as in polluted land and water surfaces through bioremediation. The embodiments herein can be deployed for agile expedient manufacturing of specialty materials or point of need manufacturing including commercial and military technology. For example, in military applications, the techniques provided by the embodiments herein may be utilized for medical and/or pharmaceutical purposes related to the well-being of soldiers, or for decontamination of military environments. Moreover, the embodiments herein may provide for the modulation of microbiomes to increase soldier performance.

The embodiments herein allow for fine-tuned control of the production of reduced electron carriers enabling optimization of redox inputs to chemical production pathways without the need for genetic alterations. This overcomes the limitations of the conventional techniques and solutions that generally require pathway modification using metabolic engineering to optimize the availability of reduced electron carriers to improve chemical outputs, and which tend to be laborious efforts that do not guarantee a desired output. Accordingly, the ability to use native pathways to exert metabolic control via co-feeding, as provided by the embodiments herein, decreases the risks and costs associated with metabolic engineering.

Furthermore, the embodiments herein for modulating the cells redox environment may be applicable in genetic engineering, the addition of gasses such as $O_2$ and $H_2$, the addition of exogenous electron carriers, the interaction of cells with electrodes, changing substrates, and changing the growth environment, according to some examples. Additionally, the embodiments herein may be used for the manufacturing of desired industrial chemicals through the manipulation of metabolic state of bacteria via controlled regeneration of reduced electron carriers. Also, the metabolic flux control for pharmaceutical production of both small and large molecules can be accomplished using the techniques provided by the embodiments herein. As such, the selective metabolic switching of bacteria within the consortia for chemical production or improved health and performance can be achieved. Host pathway optimization as provided by the embodiments herein can further allow for tailored production of desirable products including chemicals, energetic molecules, hierarchical materials, and plastics.

The embodiments herein control the metabolic state of cells via controlled regeneration of reduced electron carriers for chemical production using co-feeding of substrates with two different oxidation states. Metabolism of galacturonate (i.e., a more oxidized substrate) results in the production of less reduced electron carriers, such as NADH and NADPH, when compared to the metabolism of carbohydrates (i.e., a more reduced substrate). The co-utilization of galacturonate (or its polymers) and carbohydrates produces an intermediate amount of reduced electron carriers. Altering the ratio (i.e., in terms of molar concentration) of the galacturonate (or its polymers) and the carbohydrate allows for fine-tuned control of reduced electron carrier production, which is used to direct metabolic processes. Accordingly, these processes can be used to produce chemicals from natural and synthetic pathways, and reduce the production of undesirable side-products.

The foregoing description of the specific embodiments will so fully reveal the general nature of the embodiments herein that others may, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein may be practiced with modification within the spirit and scope of the appended claims.

The invention claimed is:

1. A method of controlling a metabolic process, the method comprising:
    providing an anaerobic organism;
    providing a first chemical substrate comprising a first oxidation state;
    providing a second chemical substrate comprising a second oxidation state, wherein the first oxidation state is different from the second oxidation state;
    co-feeding the first chemical substrate and the second chemical substrate at a predetermined mixture ratio to the anaerobic organism to primarily produce an optimized yield of a first chemical;
    controlling regeneration of reduced electron carriers in cells of the anaerobic organism caused by the anaerobic organism's metabolism of co-utilization of the first chemical substrate and the second chemical substrate through alteration of the ratio of the mixture of the first chemical substrate and the second chemical substrate from the predetermined mixture ratio; and
    altering chemical production of the anaerobic organism by sequentially co-feeding the first chemical substrate and the second chemical substrate at the altered mixture ratio to the anaerobic organism to primarily produce an optimized yield of a second chemical.

2. The method of claim 1, wherein the anaerobic organism comprises a fermentative organism.

3. The method of claim 1, wherein the first chemical substrate and the second chemical substrate are selected from the group consisting of: galacturonate, gluconate, glucose, mannitol and glycerol.

4. The method of claim 1, wherein one or both of the first chemical substrate and the second chemical substrate comprise a carbohydrate.

5. The method of claim 4, wherein the carbohydrate comprises any of glucose, mannose, galactose, fructose, arabinose, xylose, sucrose, lactose, maltose, cellobiose, and starch.

6. The method of claim 1, wherein the reduced electron carriers comprise any of NADH, NADPH, thioredoxins, and ferrodoxins.

7. The method of claim 1, wherein one of the predetermined mixture ratio or altered mixture ratio comprises a substantially equal proportion of the first chemical substrate and the second chemical substrate.

8. The method of claim 1, wherein the anaerobic organism comprises *Clostridium acetobutylicum* or *Clostridium saccharoperbutylacetonicum*.

9. A method of controlling a fermentation process, the method comprising:
    providing a fermentative organism;
    co-feeding the fermentative organism with a mixture of at least two feedstock materials at a first ratio thereof to primarily produce a first chemical;
    controlling a fermentation process of the fermentative organism by altering the first ratio of the at least two feedstock materials to a second ratio thereof; and
    altering chemical production of the fermentative organism by sequentially co-feeding the fermentative organism with a mixture of at least the two feedstock materials at the second ratio to primarily produce a second chemical.

10. The method of claim 9, wherein the fermentative organism co-utilizes the at least two feedstock materials in the fermentation process to some degree simultaneously.

11. The method of claim 9, co-feeding one of the at least two feedstock materials from an onset of fermentation until one of the at least two feedstock materials is depleted, and subsequently co-feeding another of the at least two feedstock materials.

12. The method of claim 9, wherein the fermentation process co-utilizes the at least two feedstock materials in an oxidized or reduced form.

13. The method of claim 9, wherein the first and second chemicals are selected from the group consisting of: lactate, acetoin, acetate, ethanol, butyrate and butanol.

14. The method of claim 9, wherein the at least two feedstock materials are selected from the group consisting of: galacturonate, gluconate, glucose, mannitol and glycerol.

15. The method of claim 9, wherein the at least two feedstock materials comprise a carbohydrate feedstock and another feedstock having an oxidation state different from the carbohydrate.

16. The method of claim 9, wherein one of the first ratio and the second ratio comprises a substantially equal ratio of the at least two feedstock materials.

17. The method of claim 9, wherein the first ratio and the second ratio of the at least two feedstock materials are selected from the group consisting of: 25% glucose and 75% galacturonic acid; 25% glucose and 75% gluconic acid; 50% galacturonic acid and 50% gluconic acid; 50% glucose and 50% galacturic acid; 50% glucose and 50% gluconic acid; 50% glucose and 50% galacturonic acid; 75% glucose and 25% galacturonic acid; and 75% glucose and 25% gluconic acid.

\* \* \* \* \*